United States Patent
Veyland et al.

(10) Patent No.: US 9,187,620 B2
(45) Date of Patent: *Nov. 17, 2015

(54) RUBBER COMPOSITION COMPRISING A THIADIAZOLE

(75) Inventors: Anne Veyland, Marsat (FR); Nicolas Seeboth, Clermont-Ferrand (FR); Jose Carlos Araujo Da Silva, Pont du Chateau (FR)

(73) Assignees: COMPAGNIE GENERALE DES ETABLISSEMENTS MICHELIN, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,090

(22) PCT Filed: Oct. 8, 2010

(86) PCT No.: PCT/EP2010/065072
§ 371 (c)(1),
(2), (4) Date: Sep. 25, 2012

(87) PCT Pub. No.: WO2011/042525
PCT Pub. Date: Apr. 14, 2011

(65) Prior Publication Data
US 2013/0053510 A1     Feb. 28, 2013

(30) Foreign Application Priority Data

Oct. 8, 2009     (FR) .................................... 09 57039

(51) Int. Cl.
| | |
|---|---|
| *C08L 7/00* | (2006.01) |
| *C08K 5/46* | (2006.01) |
| *B60C 1/00* | (2006.01) |
| *C07D 285/125* | (2006.01) |
| *C08K 5/00* | (2006.01) |
| *C08K 5/47* | (2006.01) |
| *C08L 9/06* | (2006.01) |

(52) U.S. Cl.
CPC ... *C08K 5/46* (2013.01); *B60C 1/00* (2013.01); *C07D 285/125* (2013.01); *C08K 5/0025* (2013.01); *C08K 5/47* (2013.01); *C08L 9/06* (2013.01)

(58) Field of Classification Search
CPC ...... B60C 1/00; C07D 285/04; C08K 5/0025; C08K 5/46; C08K 5/47; C08L 21/00; C08L 9/06
USPC .......................... 524/575.5; 525/332.6, 332.7
See application file for complete search history.

(56) References Cited

U.S. PATENT DOCUMENTS

| | | | |
|---|---|---|---|
| 3,899,502 A | | 8/1975 | Harman |
| 5,151,468 A | * | 9/1992 | Nakajima et al. .......... 525/332.7 |
| 2004/0176504 A1 | * | 9/2004 | Karol et al. ...................... 524/84 |
| 2005/0016650 A1 | * | 1/2005 | Durel et al. ................ 152/209.1 |

FOREIGN PATENT DOCUMENTS

| | | | |
|---|---|---|---|
| JP | 9 012782 | | 1/1997 |
| JP | 2000191865 A | * | 7/2000 |
| JP | 2007254496 A | * | 10/2007 |

OTHER PUBLICATIONS

JP 2007-254496 A (2007), machine translation, JPO Advanced Industrial Property Network (AIPN).*
Minigawa et al. (JP 2000-191865 A, machine translation, Japan Patents Fulltext [retrieved Dec. 19, 2014]. Retrieved from: ProQuest Dialog. Accession. No. JP2000191865A).*

* cited by examiner

*Primary Examiner* — Susannah Chung
*Assistant Examiner* — Josephine Chang
(74) *Attorney, Agent, or Firm* — Cozen O'Connor

(57) ABSTRACT

A rubber composition for the manufacture of tires, based on one or more diene elastomers, on one or more reinforcing fillers and on a vulcanization system, characterized in that the said vulcanization system comprises one or more thiadiazole compounds of formula:

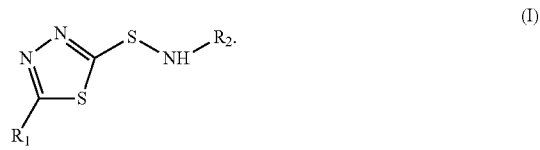

(I)

18 Claims, No Drawings

RUBBER COMPOSITION COMPRISING A THIADIAZOLE

RELATED APPLICATIONS

This application is a U.S. National Phase Application under 35 USC 371 of International Application No. PCT/EP2010/065072, filed on Oct. 8, 2010.

This patent application claims the priority of the French patent application no. 09/57039 filed Oct. 8, 2009, the disclosure content of which is hereby incorporated by reference.

FIELD OF THE INVENTION

The present invention relates to a rubber composition which can be used in particular in the manufacture of tires or semi-finished products for tires, such as treads, the said composition being based on a diene elastomer, on a reinforcing filler and on a vulcanization system comprising a specific thiadiazole compound.

BACKGROUND OF THE INVENTION

The vulcanization of diene elastomers by sulphur is widely used in the rubber industry, in particular in the tire industry. Use is made, to vulcanize diene elastomers, of a relatively complex vulcanization system comprising, in addition to sulphur, a primary vulcanization accelerator, such as sulphenamides comprising a benzothiazole ring system, and various secondary vulcanization accelerators or vulcanization activators, very particularly zinc derivatives, such as zinc oxide (ZnO), alone or used with fatty acids.

The sulphenamides comprising a benzothiazole ring system used as primary vulcanization accelerators are, for example, N-cyclohexyl-2-benzothiazolesulphenamide (abbreviated to "CBS"), N,N-dicyclohexyl-2-benzothiazolesulphenamide (abbreviated to "DCBS"), N-tert-butyl-2-benzothiazolesulphenamide (abbreviated to "TBBS") and the mixtures of these compounds.

The rubber compositions have to exhibit satisfactory crosslinking while retaining an acceptable compromise between the different rheometric properties.

SUMMARY OF THE INVENTION

The inventors have discovered a novel rubber composition comprising, as vulcanization accelerator, a novel thiadiazole compound. This novel rubber composition makes it possible to obtain a compromise in rheometric properties similar to that obtained with rubber compositions comprising vulcanization accelerators conventionally used.

One aspect of the invention is directed to a rubber composition for the manufacture of tires, based on one or more diene elastomers, on one or more reinforcing fillers and on a vulcanization system, the said vulcanization system comprising one or more thiadiazole compounds of formula:

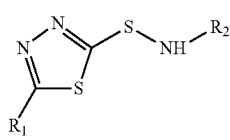

(I)

where $R_1$ represents independently H or a $C_1$-$C_{25}$-hydrocarbon group chosen from linear, branched or cyclic alkyl groups and aryl groups, optionally interrupted by one or more heteroatoms, $R_2$ represents:
a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Another aspect of the invention is a process for preparing a rubber composition for the manufacture of tires made in accordance with an embodiment of the invention, characterized in that it comprises the following stages:

incorporating the reinforcing filler or fillers in the diene elastomer or elastomers, during a first "non-productive" stage, everything being kneaded thermomechanically, in one or more goes, until a maximum temperature of between 130° C. and 200° C. is reached, cooling the combined mixture to a temperature of less than 100° C., subsequently incorporating, during a second "productive" stage, the vulcanization system and then kneading everything up to a maximum temperature of less than 120° C.

Another aspect of the invention is directed to the use of a composition according to an embodiment of the invention in the manufacture of a finished article or a semi-finished product intended for a motor vehicle ground-contact system, such as tire, internal tire safety support, wheel, rubber spring, elastomeric joint or other suspension and anti-vibratory element. In particular, the composition according to an embodiment of the invention can be used in the manufacture of semi-finished rubber products intended for tires, such as treads, crown reinforcing plies, sidewalls, carcass reinforcing plies, beads, protectors, underlayers, rubber blocks and other internal rubbers, in particular decoupling rubbers, intended to provide the bonding or the interface between the abovementioned regions of the tires.

A further aspect of the invention is directed to a finished article or semi-finished product intended for a motor vehicle ground-contact system, in particular the tires and semi-finished products for tires comprising a composition according to an embodiment of the invention. The tires in accordance with the invention are intended in particular for passenger vehicles as for industrial vehicles chosen from vans, heavy-duty vehicles—i.e., underground, bus, heavy road transport vehicles (lorries, tractors, trailers) or off-road vehicles—, agricultural vehicles or earth-moving equipment, air-craft, or other transportation or handling vehicles.

A final aspect of the invention is directed to the use as vulcanization accelerator, in a composition based on one or more diene elastomers, on one or more reinforcing fillers and on a vulcanization system, of one or more thiadiazole compounds of formula (I).

DETAILED DISCUSSION

The invention and its advantages will be easily understood in the light of the description and implementation examples which follow.

I. Measurements and Tests Used

The rubber compositions, in which the thiadiazole vulcanization accelerators are tested, are characterized, before and after curing, as indicated below.

Rheometry

The measurements are carried out at 150° C. with an oscillating disc rheometer, according to Standard DIN 53529—part 3 (June 1983). The change in the rheometric torque, $\Delta$Torque, as a function of time describes the change in the stiffening of the composition as a result of the vulcanization reaction. The measurements are processed according to Standard DIN 53529—part 2 (March 1983): $t_0$ is the induction period, that is to say the time necessary for the start of the vulcanization reaction; $t_\alpha$ (for example $t_{99}$) is the time necessary to achieve a conversion of $\alpha$ %, that is to say $\alpha$ % (for example 99%) of the difference between the minimum and maximum torques. The conversion rate constant, denoted K (expressed in $min^{-1}$), which is 1st order, calculated between 30% and 80% conversion, which makes it possible to assess the vulcanization kinetics, is also measured.

II. Conditions for the Implementation of the Invention

As explained above, the composition according to the invention is based on one or more diene elastomers, on one or more reinforcing fillers and on a vulcanization system.

The expression composition "based on" should be understood as meaning a composition comprising the mixture and/or the reaction product of the various constituents used, some of these base constituents being capable of reacting or intended to react with one another, at least in part, during the various phases of manufacture of the composition, in particular during its vulcanization.

In the present description, unless expressly indicated otherwise, all the percentages (%) are % by weight. Moreover, any interval of values denoted by the expression "between a and b" represents the range of values extending from greater than a to less than b (i.e., limits a and b excluded), whereas any interval of values denoted by the expression "from a to b" means the range of values extending from a up to b (i.e., including the strict limits a and b).

II-1. Diene Elastomer

The term "diene" elastomer or rubber should be understood as meaning, in a known way, an elastomer resulting at least in part (i.e., a homopolymer or a copolymer) from diene monomers (monomers carrying two carbon-carbon double bonds which may or may not be conjugated).

These diene elastomers can be classified into two categories: "essentially unsaturated" or "essentially saturated". The term "essentially unsaturated" is understood to mean generally a diene elastomer resulting at least in part from conjugated diene monomers having a level of units of diene origin (conjugated dienes) which is greater than 15% (molar %); thus it is that diene elastomers such as butyl rubbers or copolymers of dienes and of α-olefins of EPDM type do not come within the preceding definition and can in particular be described as "essentially saturated" diene elastomers (low or very low level of units of diene origin, always less than 15%). In the category of "essentially unsaturated" diene elastomers, the term "highly unsaturated" diene elastomer is understood to mean in particular a diene elastomer having a level of units of diene origin (conjugated dienes) which is greater than 50%.

Given these definitions, the term diene elastomer capable of being used in the compositions in accordance with the invention is understood more particularly to mean:

(a) any homopolymer obtained by polymerization of a conjugated diene monomer having from 4 to 12 carbon atoms;

(b) any copolymer obtained by copolymerization of one or more conjugated dienes with one another or with one or more vinylaromatic compounds having from 8 to 20 carbon atoms;

(c) a ternary copolymer obtained by copolymerization of ethylene and of an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d) a copolymer of isobutene and of isoprene (butyl rubber) and also the halogenated versions, in particular chlorinated or brominated versions, of this type of copolymer.

Although it applies to any type of diene elastomer, a person skilled in the art of tires will understand that the present invention is preferably employed with essentially unsaturated diene elastomers, in particular of the type (a) or (b) above.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene. The following, for example, are suitable as vinylaromatic compounds: styrene, ortho-, meta- or para-methylstyrene, the "vinyltoluene" commercial mixture, para-(tert-butyl)styrene, methoxystirenes, chlorostirenes, vinylmesitylene, divinylbenzene or vinylnaphthalene.

The copolymers can comprise between 99% and 20% by weight of diene units and between 1% and 80% by weight of vinylaromatic units. The elastomers can have any microstructure which depends on the polymerization conditions used, in particular on the presence or absence of a modifying and/or randomizing agent and on the amounts of modifying and/or randomizing agent employed. The elastomers can, for example, be block, random, sequential or microsequential elastomers and can be prepared in dispersion, in emulsion or in solution; they can be coupled and/or star-branched or also functionalized with a coupling and/or star-branching or functionalization agent. For coupling with carbon black, mention may be made, for example, of functional groups comprising a C—Sn bond or of aminated functional groups, such as aminobenzophenone, for example; for coupling with a reinforcing inorganic filler, such as silica, mention may be made, for example, of silanol functional groups or polysiloxane functional groups having a silanol end (such as described, for example, in FR 2 740 778, U.S. Pat. No. 6,013,718 or WO 2008/141702), of alkoxysilane groups (such as described, for example, in FR 2 765 882 or U.S. Pat. No. 5,977,238), of carboxyl groups (such as described, for example, in WO 01/92402, U.S. Pat. No. 6,815,473, WO 2004/096865 or U.S. 2006/0089445) or of polyether groups (such as described, for example, in EP 1 127 909, U.S. Pat. No. 6,503,973, WO 2009/000750 or WO 2009/000752). Mention may also be made, as other examples of functionalized elastomers, of elastomers (such as SBR, BR, NR or IR) of the epoxidized type.

The following are suitable: polybutadienes, in particular those having a content (molar %) of 1,2-units of between 4% and 80% or those having a content (molar %) of cis-1,4-units of greater than 80%, polyisoprenes, butadiene/styrene copolymers, and in particular those having a Tg (glass transition temperature, measured according to ASTM D3418) of between 0° C. and −70° C. and more particularly between −10° C. and −60° C., a stirene content of between 5% and 60% by weight and more particularly between 20% and 50%, a content (molar %) of 1,2-bonds of the butadiene part of between 4% and 75% and a content (molar %) of trans-1,4-bonds of between 10% and 80%, butadiene/isoprene copolymers, in particular those having an isoprene content of between 5% and 90% by weight and a Tg of −40° C. to −80° C., or isoprene/stirene copolymers, in particular those having a stirene content of between 5% and 50% by weight and a Tg of between 5° C. and −50° C. In the case of butadiene/stirene/isoprene copolymers, those having a stirene content of between 5% and 50% by weight and more particularly of between 10% and 40%, an isoprene content of between 15% and 60% by weight and more particularly of between 20% and 50%, a butadiene content of between 5% and 50% by weight and more particularly of between 20% and 40%, a content (molar %) of 1,2-units of the butadiene part of between 4% and 85%, a content (molar %) of trans-1,4-units of the butadiene part of between 6% and 80%, a content (molar %) of 1,2- plus 3,4-units of the isoprene part of between 5% and 70% and a content (molar %) of trans-1,4-units of the isoprene part of between 10% and 50%, and more generally any butadiene/stirene/isoprene copolymer having a Tg of between −5° C. and −70° C., are suitable in particular.

To sum up, the diene elastomer or elastomers of the composition according to the invention are preferably chosen from the group of the highly unsaturated diene elastomers consisting of polybutadienes (abbreviated to "BR"), synthetic polyisoprenes (IR), natural rubber (NR), butadiene copolymers, isoprene copolymers and the mixtures of these elastomers. Such copolymers are more preferably chosen from the group consisting of butadiene/stirene copolymers (SBR), isoprene/butadiene copolymers (BIR), isoprene/stirene copolymers (SIR) and isoprene/butadiene/stirene copolymers (SBIR).

Preferably, the diene elastomer is natural rubber.

According to a specific embodiment, the diene elastomer is predominantly (i.e., for more than 50 phr) an SBR, whether an SBR prepared in emulsion ("ESBR") or an SBR prepared in solution ("SSBR"), or an SBR/BR, SBR/NR (or SBR/IR), BR/NR (or BR/IR) or also. SBR/BR/NR (or SBR/BR/IR) blend (mixture). In the case of an SBR (ESBR or SSBR) elastomer, use is made in particular of an SBR having a moderate stirene content, for example of between 20% and 35% by weight, or a high stirene content, for example from 35% to 45%, a content of vinyl bonds of the butadiene part of between 15% and 70%, a content (molar %) of trans-1,4-bonds of between 15% and 75% and a Tg of between −10° C. and −55° C.; such an SBR can advantageously be used as a mixture with a BR preferably having more than 90% (molar %) of cis-1,4-bonds.

According to another specific embodiment, the diene elastomer is predominantly (for more than 50 phr) an isoprene elastomer. This is the case in particular when the compositions of the invention are intended to constitute, in the tires, rubber matrices of certain treads (for example for industrial vehicles), of crown reinforcing plies (for example of working plies, protection plies or hooping plies), of carcass reinforcing plies, of sidewalls, of beads, of protectors, of underlayers, of rubber blocks and other internal rubbers providing the interface between the abovementioned regions of the tires.

The term "isoprene elastomer" is understood to mean, in a known way, an isoprene homopolymer or copolymer, in other words a diene elastomer chosen from the group consisting of natural rubber (NR), synthetic polyisoprenes (IR), the various copolymers of isoprene and the mixtures of these elastomers. Mention will in particular be made, among isoprene copolymers, of isobutene/isoprene copolymers (butyl rubber—IIR), isoprene/stirene copolymers (SIR), isoprene/butadiene copolymers (BIR) or isoprene/butadiene/stirene copolymers (SBIR). This isoprene elastomer is preferably natural rubber or a synthetic cis-1,4-polyisoprene; use is preferably made, among these synthetic polyisoprenes, of the polyisoprenes having a level (molar %) of cis-1,4-bonds of greater than 90%, more preferably still of greater than 98%.

According to another specific embodiment, in particular when it is intended for a tire sidewall or for an airtight internal rubber of a tubeless tire (or other air-impermeable component), the composition in accordance with the invention can comprise at least one essentially saturated diene elastomer, in particular at least one EPDM copolymer or one butyl rubber (optionally chlorinated or brominated), whether these copolymers are used alone or as a mixture with highly unsaturated diene elastomers as mentioned above, in particular NR or IR, BR or SBR.

According to another preferred embodiment of the invention, the rubber composition comprises a blend of a (one or more) "high Tg" diene elastomer exhibiting a Tg of between −70° C. and 0° C. and of a (one or more) "low Tg" diene elastomer exhibiting a Tg of between −110° C. and −80° C., more preferably between −105° C. and −90° C. The high Tg elastomer is preferably chosen from the group consisting of S-SBRs, E-SBRs, natural rubber, synthetic polyisoprenes (exhibiting a level (molar %) of cis-1,4-structures preferably of greater than 95%), BIRs, SIRs, SBIRs and the mixtures of these elastomers. The low Tg elastomer preferably comprises butadiene units according to a level (molar %) at least equal to 70%; it preferably consists of a polybutadiene (BR) exhibiting a level (molar %) of cis-1,4-structures of greater than 90%.

According to another specific embodiment of the invention, the rubber composition comprises, for example, from 30 to 100 phr, in particular from 50 to 100 phr, of a high Tg elastomer as a blend with 0 to 70 phr, in particular from 0 to 50 phr, of a low Tg elastomer; according to another example, it comprises, for the whole of the 100 phr, one or more SBR(s) prepared in solution.

According to another specific embodiment of the invention, the diene elastomer of the composition according to the invention comprises a blend of a BR (as low Tg elastomer) exhibiting a level (molar %) of cis-1,4-structures of greater than 90% with one or more S-SBRs or E-SBRs (as high Tg elastomer(s)).

The composition according to the invention can comprise a single diene elastomer or a mixture of several diene elastomers, it being possible for the diene elastomer or elastomers to be used in combination with any type of synthetic elastomer other than a diene elastomer, indeed even with polymers other than elastomers, for example thermoplastic polymers.

II-2. Reinforcing Filler

Use may be made of any type of reinforcing filler known for its capabilities of reinforcing a rubber composition which can be used in the manufacture of tires, for example an organic filler, such as carbon black, a reinforcing inorganic filler, such as silica, or a blend of these two types of filler, in particular a blend of carbon black and silica.

All carbon blacks, in particular blacks of the HAF, ISAF or SAF type, conventionally used in tires ("tire-grade" blacks) are suitable as carbon blacks. Mention will more particularly be made, among the latter, of the reinforcing carbon blacks of the 100, 200 or 300 series (ASTM grades), such as, for example, the N115, N134, N234, N326, N330, N339, N347 or N375 blacks, or also, depending on the applications targeted, the blacks of higher series (for example, N660, N683 or N772). The carbon blacks might, for example, be already incorporated in the isoprene elastomer in the form of a masterbatch (see, for example, Applications WO 97/36724 or WO 99/16600).

Mention may be made, as examples of organic fillers other than carbon blacks, of the functionalized polyvinylaromatic organic fillers as described in Applications WO-A-2006/069792 and WO-A-2006/069793.

The term "reinforcing inorganic filler" should be understood, in the present patent application, by definition, as meaning any inorganic or mineral filler, whatever its colour and its origin (natural or synthetic), also known as "white filler", "clear filler" or even "non-black filler", in contrast to carbon black, capable of reinforcing by itself alone, without means other than an intermediate coupling agent, a rubber composition intended for the manufacture of tires, in other words capable of replacing, in its reinforcing role, a conventional tire-grade carbon black; such a filler is generally characterized, in a known way, by the presence of hydroxyl (—OH) groups at its surface.

The physical state under which the reinforcing inorganic filler is provided is not important, whether it is in the form of a powder, of microbeads, of granules, of beads or any other appropriate densified form. Of course, the term reinforcing inorganic filler is also understood to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are suitable in particular as reinforcing inorganic fillers. The silica used can be any reinforcing silica known to a person skilled in the art, in particular any precipitated or pyrogenic silica exhibiting a BET surface and a CTAB specific surface both of less than 450 m$^2$/g, preferably from 30 to 400 m$^2$/g. Mention will be made, as highly dispersible ("HDS") precipitated silicas, for example, of the Ultrasil 7000 and Ultrasil 7005 silicas from Degussa, the Zeosil 1165MP, 1135MP and 1115MP silicas from Rhodia, the Hi-Sil EZ150G silica from PPG, the Zeopol 8715, 8745 and 8755 silicas from Huber or the silicas with a high specific surface as described in Application WO 03/16837.

When the composition according to the invention is intended for tire treads having a low rolling resistance, the reinforcing inorganic filler used, in particular if it is silica, preferably has a BET surface of between 45 and 400 m$^2$/g, more preferably of between 60 and 300 m$^2$/g.

Preferably, the level of total reinforcing filler (carbon black and/or reinforcing inorganic filler, such as silica) is between 20 and 200 phr, more preferably between 30 and 150 phr, the optimum being in a known way different depending on the specific applications targeted: the level of reinforcement expected with regard to a bicycle tire, for example, is, of course, less than that required with regard to a tire capable of running at high speed in a sustained manner, for example a motorcycle tire, a tire for a passenger vehicle or a tire for a utility vehicle, such as a heavy duty vehicle.

According to one embodiment of the invention, use is made of a reinforcing filler comprising between 30 and 150 phr, more preferably between 50 and 120 phr, of inorganic filler, particularly silica, and optionally carbon black; the carbon black, when it is present, is preferably used at a level of less than 20 phr, more preferably of less than 10 phr (for example, between 0.1 and 10 phr).

According to another embodiment, the reinforcing filler is carbon black.

In order to couple the reinforcing inorganic filler to the diene elastomer, use is made, in a known way, of an at least bifunctional coupling agent (or bonding agent) intended to provide a satisfactory connection, of chemical and/or physical nature, between the inorganic filler (surface of its particles) and the diene elastomer, in particular bifunctional organosilanes or polyorganosiloxanes.

Use is made in particular of silane polysulphides, referred to as "symmetrical" or "unsymmetrical" depending on their specific structure, as described, for example, in Applications WO 03/002648 (or U.S. 2005/016651) and WO 03/002649 (or US 2005/016650).

"Symmetrical" silane polysulphides corresponding to the following general formula (III):

$$Z-A-S_x-A-Z, \quad (III)$$

in which:
x is an integer from 2 to 8 (preferably from 2 to 5);
A is a divalent hydrocarbon radical (preferably, $C_1$-$C_{18}$ alkylene groups or $C_6$-$C_{12}$ arylene groups, more particularly $C_1$-$C_{10}$, in particular $C_1$-$C_4$, alkylenes, especially propylene);
Z corresponds to one of the formulae below:

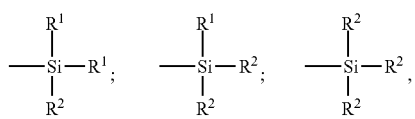

in which:
the $R^1$ radicals, which are unsubstituted or substituted and identical to or different from one another, represent a $C_1$-$C_{18}$ alkyl, $C_5$-$C_{18}$ cycloalkyl or $C_6$-$C_{18}$ aryl group (preferably, $C_1$-$C_6$ alkyl, cyclohexyl or phenyl groups, in particular $C_1$-$C_4$ alkyl groups, more particularly methyl and/or ethyl),
the $R^2$ radicals, which are unsubstituted or substituted and identical to or different from one another, represent a $C_1$-$C_{18}$ alkoxyl or $C_5$-$C_{18}$ cycloalkoxyl group (preferably a group chosen from $C_1$-$C_8$ alkoxyls and $C_5$-$C_8$ cycloalkoxyls, more preferably still a group chosen from $C_1$-$C_4$ alkoxyls, in particular methoxyl and ethoxyl),
are suitable in particular, without the above definition being limiting.

In the case of a mixture of alkoxysilane polysulphides corresponding to the above formula (III), in particular the usual mixtures available commercially, the mean value of the "x" index is a fractional number preferably of between 2 and 5, more preferably in the vicinity of 4. However, the invention can also advantageously be carried out, for example, with alkoxysilane disulphides (x=2).

Mention will more particularly be made, as examples of silane polysulphides, of bis(($C_1$-$C_4$)alkoxyl($C_1$-$C_4$)alkylsilyl ($C_1$-$C_4$)alkyl)polysulphides (in particular disulphides, trisulphides or tetrasulphides), such as, for example, bis(3-trimethoxysilylpropyl) or bis(3-triethoxysilylpropyl) polysulphides. Use is in particular made, among these compounds, of bis(3-triethoxysilylpropyl)tetrasulphide, abbreviated to TESPT, of formula [($C_2H_5O)_3Si(CH_2)_3S_2]_2$, or bis(triethoxysilylpropyl)disulphide, abbreviated to TESPD, of formula [($C_2H_5O)_3Si(CH_2)_3S]_2$. Mention will also be made, as preferred examples, of bis(mono($C_1$-$C_4$) alkoxyldi($C_1$-$C_4$)alkylsilylpropyl)polysulphides (in particular disulphides, trisulphides or tetrasulphides), more particularly bis(monoethoxydimethylsilylpropyl)tetrasulphide, as described in Patent Application WO 02/083782 (or U.S. 2004/132880).

Mention will in particular be made, as coupling agent other than alkoxysilane polysulphide, of bifunctional POSs (polyorganosiloxanes) or of hydroxysilane polysulphides ($R^2$=OH in the above formula III), such as described in Patent Applications WO 02/30939 (or U.S. Pat. No. 6,774,255) and WO 02/31041 (or U.S. 2004/051210), or of silanes or POSs carrying azodicarbonyl functional groups, such as described, for example, in Patent Applications WO 2006/125532, WO 2006/125533 and WO 2006/125534.

In the rubber compositions in accordance with the invention, the content of coupling agent is preferably between 4 and 12 phr, more preferably between 3 and 8 phr.

A person skilled in the art will understand that a reinforcing filler of another nature, in particular organic nature, might be used as filler equivalent to the reinforcing inorganic filler described in the present section, provided that this reinforcing filler is covered with an inorganic layer, such as silica, or else comprises, at its surface, functional sites, in particular hydroxyls, requiring the use of a coupling agent in order to form the connection between the filler and the elastomer.

II.3 Vulcanization System

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine), incorporated during the first non-productive phase and/or during the productive phase, as described subsequently.

The sulphur is used at a preferred level of between 0.5 and 10 phr, more preferably of between 0.5 and 5 phr, in particular between 0.5 and 3 phr, when the composition of the invention is intended, according to a preferred form of the invention, to constitute a tire tread.

The primary vulcanization accelerator must make possible crosslinking of the rubber compositions within industrially acceptable times, while retaining a minimum safety period ("scorch time") during which the compositions can be shaped without the risk of premature vulcanization ("scorching").

According to the invention, the vulcanization system comprises, as primary vulcanization accelerator, one or more thiadiazole compounds of formula:

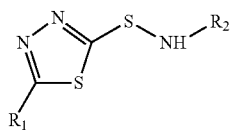

(I)

where $R_1$ represents independently H or a $C_1$-$C_{25}$-hydrocarbon group chosen from linear, branched or cyclic alkyl groups and aryl groups, optionally interrupted by one or more heteroatoms, $R_2$ represents:
a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

The compounds of formula (I) can advantageously replace, in all or part, the sulphenamide compounds conventionally used.

The term cyclic alkyl group is understood to mean an alkyl group composed of one or more rings.

The heteroatom or heteroatoms can be a nitrogen, sulphur or oxygen atom.

Preferably, the thiadiazole compound of formula (I) is such that:

$R_1$ represents H or a $C_1$-$C_{25}$-hydrocarbon group chosen from linear, branched or cyclic alkyl groups and aryl groups, optionally interrupted by one or more heteroatoms, $R_2$ represents:
a linear $C_2$-$C_{25}$ alkyl or branched $C_3$ or $C_5$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

According to a first embodiment, $R_1$ represents a methyl group.

According to a second embodiment, $R_1$ represents H.

According to one embodiment, $R_2$ advantageously represents a cyclic $C_3$-$C_{10}$ alkyl group.

In particular, $R_2$ can represent a cyclohexyl group.

According to another embodiment, $R_2$ represents a tert-butyl group.

Preferably, $R_2$ represents a cyclohexyl group.

Thus, a preferred compound of formula (I) is that in which $R_1$ represents H and $R_2$ represents a cyclohexyl. In this case, the thiadiazole compound of formula (I) is N-cyclohexyl-S-(1,3,4-thiadiazol-2-yl)thiohydroxylamine.

Another preferred compound of formula (I) is that in which $R_1$ represents a methyl and $R_2$ represents a cyclohexyl. In this case, the thiadiazole compound of formula (I) is N-cyclohexyl-S-(5-methyl-1,3,4-thiadiazol-2-yl)thiohydroxylamine.

The compound or compounds of formula (I) generally represent from 0.1 to 7 phr, preferably from 0.5 to 7 phr and better still from 0.5 to 5 phr.

The thiadiazole compound or compounds present in the composition according to the invention can be prepared according to the process comprising the following stages:

the starting material is compound (A) of following formula:

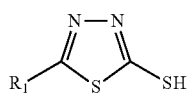

(A)

where $R_1$ is as defined above,
compound (A) is reacted with a compound of formula $R_2NH_2$, or $R_2$ is as defined above, in the presence of a base, then
an oxidizing composition comprising at least one oxidizing agent is added to the reaction medium, in order to obtain the thiadiazole of formula (I).

According to a first embodiment, $R_1$ represents hydrogen.

According to a second embodiment, $R_1$ represents a methyl group.

Preferably, $R_2$ represents a cyclohexyl group.

When compound (A) is reacted in the presence of a base, the latter can, for example, be an aqueous sodium hydroxide solution.

As explained above, the process comprises a stage of addition of an oxidizing composition. The oxidizing agent can be chosen from conventional oxidizing agents, such as bromine, chlorine or iodine or also hypobromic acid, hypochloric acid or hypoiodic acid or alternatively the alkali metal salts of the above acids. Generally, an aqueous sodium hypochlorite solution is preferred.

The vulcanization system of the composition according to the invention can also comprise one or more additional primary accelerators, in particular the compounds of the family of the thiurams, zinc dithiocarbamate derivatives or thiophosphates.

II-4. Various Additives

The rubber composition according to the invention can also comprise all or a portion of the normal additives generally used in elastomer compositions intended for the manufacture of tires, in particular treads, such as, for example, plasticizing agents or extending oils, whether the latter are aromatic or non-aromatic in nature, pigments, protection agents, such as antiozone waxes (such as Cire Ozone C32 ST), chemical antiozones, antioxidants (such as N-(1,3-dimethylbutyl)-N'-phenyl-p-phenylenediamine), antifatigue agents, reinforcing resins, methylene acceptors (for example, novolac phenolic resin) or methylene donors (for example, HMT or H3M), such as described, for example, in Application WO 02/10269.

Preferably, the composition according to the invention comprises, as preferred non-aromatic or very slightly aromatic plasticizing agent, at least one compound chosen from the group consisting of naphthenic oils, paraffinic oils, MES oils, TDAE oils, glycerol esters (in particular trioleates), plasticizing hydrocarbon resins exhibiting a high Tg preferably of greater than 30° C., and the mixtures of such compounds.

The composition according to the invention can also comprise, in addition to the coupling agents, coupling activators for the reinforcing inorganic filler or more generally processing aids capable, in a known way, by virtue of an improvement in the dispersion of the inorganic filler in the rubber matrix and of a lowering in the viscosity of the compositions, of improving their property of processing in the raw state, these agents being, for example, hydrolysable silanes, such as alkylalkoxysilanes (in particular alkyltriethoxysilanes), polyols, polyethers (for example, polyethylene glycols), primary, secondary or tertiary amines (for example, trialkanolamines), hydroxylated or hydrolysable POSs, for example α,ω-dihydroxypolyorganosiloxanes (in particular α,ω-dihydroxypolydimethylsiloxanes), or fatty acids, such as, for example, stearic acid.

II-5. Manufacture of the Rubber Compositions

The rubber composition according to the invention is manufactured in appropriate mixers using two successive preparation phases according to a general procedure well known to a person skilled in the art: a first phase of thermo-mechanical working or kneading (sometimes described as "non-productive" phase) at high temperature, up to a maximum temperature of between 130° C. and 200° C., preferably between 145° C. and 185° C., followed by a second phase of mechanical working (sometimes described as "productive" phase) at a lower temperature, typically less than 120° C., for example between 60° C. and 100° C., finishing phase during which the crosslinking or vulcanization system is incorporated.

According to a preferred embodiment of the invention, all the base constituents of the composition of the invention, with the exception of the vulcanization system, namely the reinforcing filler or fillers and the coupling agent, if appropriate, are intimately incorporated, by kneading, in the diene elastomer or in the diene elastomers during the first "non-productive" phase, that is to say that at least these various base constituents are introduced into the mixer and are thermomechanically kneaded, in a single stage or several stages, until the maximum temperature of between 130° C. and 200° C., preferably of between 145° C. and 185° C., is reached.

By way of example, the first (non-productive) phase is carried out in a single thermomechanical stage during which all the necessary constituents, the optional additional processing aids and various other additives, with the exception of the vulcanization system, are introduced into an appropriate mixer, such as a normal internal mixer. The total duration of the kneading, in this non-productive phase, is preferably between 1 and 15 min. After cooling the mixture thus obtained during the first non-productive phase, the vulcanization system is then incorporated at low temperature, generally in an external mixer, such as an open mill; everything is then mixed (productive phase) for a few minutes, for example between 2 and 15 min.

The final composition thus obtained is subsequently calendered, for example in the form of a sheet or of a plaque, in particular for characterization in the laboratory, or also extruded in the form of a rubber profiled element which can be used, for example, as a tire tread for a passenger vehicle.

III. Examples of the Implementation of the Invention

In the examples which follow, the invention is implemented with N-cyclohexyl-S-(1,3,4-thiadiazol-2-yl)thiohydroxylamine (compound B) of following formula:

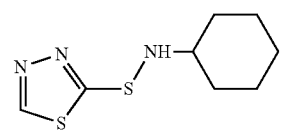 [SMILES: c1nnc(SNC2CCCCC2)s1]

III-1. Synthesis of Thiadiazole Compound B

This compound is prepared from 1,3,4-thiadiazole-2-thiol and cyclohexylamine, according to the following synthetic scheme:

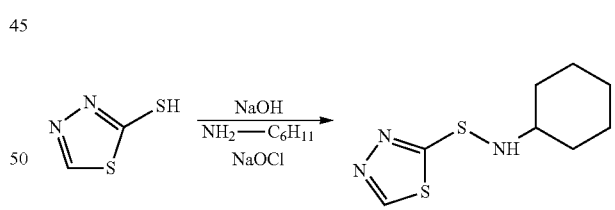

1,3,4-Thiadiazole-2-thiol is commercially available (CAS number [18686-82-3]). It can be obtained from carbon disulphide and hydrazine hydrate according to procedures described in the following documents:

1. CH 563 380 (1971)
2. FR 71 473 84 (1972)

The reaction scheme for the preparation of 1,3,4-thiadiazole-2-thiol is as follows:

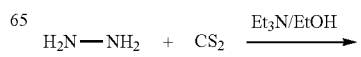

-continued

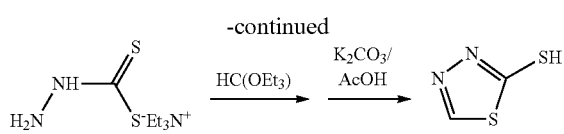

Cyclohexylamine (77.35 g, 0.78 mol) is added to a solution of 1,3,4-thiadiazole-2-thiol (18.44 g, 0.16 mol) and sodium hydroxide (14.04 g, 0.35 mol) in water (900 ml). The mixture is cooled to 0-5° C. and then the aqueous NaOCl solution (4% active chlorine) (343 ml) is added dropwise over 15 minutes. The temperature of the reaction medium is maintained between 0 and +5° C. The reaction medium is subsequently stirred at a temperature of between 0 and 5° C. for from one to one and a half hours.

Petroleum ether (100 ml) is added and the reaction medium is subsequently stirred at a temperature of between 0 and −4° C. for from 15 to 30 minutes. The precipitate is filtered off, washed with water (200 ml) and petroleum ether (50 ml) and then dried for from 2 to 3 hours under reduced pressure and for 12 hours at ambient temperature.

A white solid (11.0 g, 0.05 mol) with a melting point of 81-83° C. is obtained.

The molar purity is greater than 96% ($^1$H NMR).

The product is completely characterized by NMR. The chemical shifts obtained by $^1$H NMR in $d_6$-acetone are given in the table below. Calibration is carried out with regard to acetone (1.98 ppm in $^1$H).

| | 1 | 2 | 3 | 4 | 5 | 6 | 7 | 8 | 9 |
|---|---|---|---|---|---|---|---|---|---|
| δ $^1$H (ppm) | 9.21 | — | 4.72 | 2.81 | 1.98 / 1.19 | 1.67 / 1.25 | 1.52 / 1.14 | 1.67 / 1.25 | 1.98 / 1.19 |

III-2. Preparation of the Compositions

The procedure for the tests which follow is as follows: the diene elastomer or elastomers, the reinforcing filler or fillers and the optional coupling agent, followed, after kneading for one to two minutes, by the various other ingredients, with the exception of the vulcanization system, are introduced into an internal mixer, 70% filled and having a starting vessel temperature of approximately 90° C. Thermomechanical working (non-productive phase) is then carried out in one stage (total duration of the kneading equal to approximately 5 min), until a maximum "dropping" temperature of approximately 165° C. is reached. The mixture thus obtained is recovered and cooled, and then the vulcanization system (sulphur and thiadiazole compound) is added on an external mixer (homofinisher) at 70° C., everything being mixed (productive phase) for approximately 5 to 6 min.

The compositions thus obtained are subsequently calendered, either in the form of plaques (thickness of 2 to 3 mm) or of thin sheets of rubber, for the measurement of their physical or mechanical properties, or in the form of profiled elements which can be used directly, after cutting out and/or assembling to the desired dimensions, for example as semi-finished products for tires, in particular as tire treads.

III-3. Characterization Tests—Results

The object of this example is to compare the rheometric properties of a rubber composition, which can be used in the manufacture of a tire tread, comprising N-cyclohexyl-S-(1,3,4-thiadiazol-2-yl)thiohydroxylamine (compound B) as primary vulcanization accelerator (composition 2), with the properties of a rubber composition comprising N-cyclohexyl-2-benzothiazolesulphenamide ("CBS") (composition 1).

The formulations of the compositions are given in Table 1. The amounts are expressed as parts per 100 parts by weight of elastomer (phr).

TABLE 1

| | Composition 1 | Composition 2 |
|---|---|---|
| NR (1) | 100 | 100 |
| N220 (2) | 47.5 | 47.5 |
| Paraffin | 1 | 1 |
| TMQ (3) | 1 | 1 |
| 6-PPD (4) | 1.5 | 1.5 |
| Stearic acid | 2.5 | 2.5 |
| ZnO | 2.7 | 2.7 |
| Sulphur | 1.5 | 1.5 |
| Vulcanization accelerator | 0.6* | 0.51** |

*CBS ("Santocure CBS" from Flexsys)
**N-cyclohexyl-S-(1,3,4-thiadiazol-2-yl)thiohydroxylamine
(1) Natural rubber
(2) Carbon black
(3) TMQ: 2,2,4-trimethyl-1,2-dihydroquinoline, sold by Flexsys
(4) Antioxidant 6-p-phenylenediamine Rubber composition 2 comprising N-cyclohexyl-S-(1,3,4-thiadiazol-2-yl)thiohydroxylamine is identical to composition 1, it being understood that CBS is replaced with an isomolar amount of N-cyclohexyl-S-(1,3,4-thiadiazol-2-yl)thiohydroxylamine.

The rheometric properties at 150° C. are given in Table 2.

TABLE 2

| | Composition 1 (CBS) | Composition 2 (Compound B) |
|---|---|---|
| Rheo. prop. (DIN) | 150° C. | |
| Δtorque (dN · m) | 7.0 | 6.3 |
| k (min$^{-1}$) | 0.323 | 0.208 |
| $t_0$ (min) | 4.9 | 3.2 |
| $t_{99}$ (min) | 19.2 | 25.3 |

The rheometric properties obtained for the composition comprising N-cyclohexyl-S-(1,3,4-thiadiazol-2-yl)thiohydroxylamine are equivalent to those obtained for the composition comprising CBS. The use of N-cyclohexyl-S-(1,3,4-thiadiazol-2-yl)thiohydroxylamine makes it possible to obtain a compromise with regard to the different rheometric properties.

Furthermore, it is noted that compound B, and the compounds of formula (I) in general, advantageously replace, with regard to the environmental impact, sulphenamides comprising a mercaptobenzothiazole ring system, by not generating, in contrast to the latter, mercaptobenzothiazole on decomposing during the curing.

The invention claimed is:
1. A rubber composition for the manufacture of tires, comprising one or more diene elastomers, on one or more reinforcing fillers and a vulcanization system, wherein the vulcanization system comprises one or more thiadiazole compounds of formula:

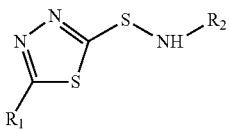 (I)

where
R₁ represents H or a $C_1$-$C_{25}$-hydrocarbon group selected from the group consisting of linear, branched or cyclic alkyl groups and aryl groups,
R₂ represents:
- a linear or branched $C_1$-$C_{25}$ alkyl group which is optionally interrupted by one or more heteroatoms selected from the group consisting of nitrogen, sulphur, and oxygen atoms and which is optionally substituted by one or more cyclic $C_3$-$C_{10}$ alkyl or $C_6$-$C_{12}$ aryl groups, or
- a cyclic $C_3$-$C_{10}$ alkyl group which is optionally interrupted by one or more heteroatoms selected from the group consisting of nitrogen, sulphur, and oxygen atoms and which is optionally substituted by one or more linear, branched or cyclic $C_1$-$C_{25}$ alkyl or $C_6$-$C_{12}$ aryl groups which are optionally interrupted by one or more heteroatoms selected from the group consisting of nitrogen, sulphur, and oxygen atoms.

2. The composition according to claim 1, wherein R₁ represents H.

3. The composition according to claim 1, wherein R₁ represents a methyl group.

4. The composition according to claim 1, wherein R₂ represents a cyclohexyl group or a tert-butyl group.

5. The composition according to claim 1, wherein the thiadiazole compound or compounds represent from 0.1 to 7 phr (parts by weight per hundred of diene elastomer).

6. The composition according to claim 1, wherein the thiadiazole compound or compounds represent 0.5 to 7 phr.

7. The composition according to claim 1, wherein the thiadiazole compound or compounds represent from 0.5 to 5 phr.

8. The composition according to claim 1, wherein the diene elastomer or elastomers are selected from the group consisting of polybutadienes, natural rubber, synthetic polyisoprenes, butadiene copolymers, isoprene copolymers and the mixtures of these elastomers.

9. The composition according to claim 8, wherein the diene elastomer is natural rubber.

10. The composition according to claim 1, wherein the reinforcing filler or fillers are selected from the group consisting of silica, carbon black and their mixtures.

11. The composition according to claim 10, wherein the reinforcing filler or fillers are carbon black.

12. The composition according to claim 1, wherein the reinforcing filler or fillers are present at a level of between 20 and 200 phr.

13. The composition according to claim 1, wherein the reinforcing filler or fillers are present at a level of between 30 and 150 phr.

14. A process for accelerating the vulcanization of a composition comprising incorporating in said composition one or more diene elastomers, one or more reinforcing fillers, and a vulcanization system comprising one or more thiadiazole compounds of formula (I) according to claim 1 as a vulcanization accelerator.

15. A process for preparing a rubber composition for the manufacture of tires according to claim 1, comprising the steps of:
incorporating the reinforcing filler or fillers in the diene elastomer or elastomers, during a non-productive stage, by thermomechanically kneading the reinforcing filler or fillers, and the diene elastomer or elastomers, until a maximum temperature of between 130° C. and 200° C. is reached,
cooling the combined mixture to a temperature of less than 100° C.,
subsequently incorporating, during a second productive phase, the vulcanization system and then
kneading the reinforcing filler or fillers, the diene elastomer or elastomers, and the vulcanization system up to a maximum temperature of less than 120° C.

16. A process for manufacturing a finished article or a semi-finished product intended for a motor vehicle ground-contact system comprising incorporating a composition according to claim 1.

17. A finished article or semi-finished product intended for a motor vehicle ground-contact system, comprising a composition according to claim 1.

18. A tire, comprising a rubber composition as defined in claim 1.

* * * * *